United States Patent [19]
Oberlander et al.

[11] Patent Number: 5,866,295
[45] Date of Patent: Feb. 2, 1999

[54] PHOTOSENSITIVE QUINOLONE COMPOUNDS AND A PROCESS OF PREPARATION

[75] Inventors: Joseph E. Oberlander, Phillipsburg; Dana L. Durham; Dinesh N. Khanna, both of Flemington, all of N.J.

[73] Assignee: Clariant Finance (BVI) Limited, Virgin Islands (Br.)

[21] Appl. No.: 813,167

[22] Filed: Mar. 7, 1997

[51] Int. Cl.[6] .............................. G03C 1/52; C08G 59/00
[52] U.S. Cl. ...................... 430/168; 430/169; 430/189; 430/190; 528/99; 534/558; 534/561; 546/156; 546/159; 546/171; 546/177
[58] Field of Search ................ 528/99; 430/168, 430/169, 189, 190; 534/558, 561; 546/156, 159, 171, 177

[56] References Cited

U.S. PATENT DOCUMENTS

| | | | |
|---|---|---|---|
| 4,339,552 | 7/1982 | Lindemann | 524/459 |
| 4,588,670 | 5/1986 | Kelly et al. | 430/165 |
| 4,601,969 | 7/1986 | Clecak et al. | 430/192 |
| 4,622,283 | 11/1986 | Gray | 430/191 |
| 4,735,885 | 4/1988 | Hopf et al. | 430/192 |
| 4,853,315 | 8/1989 | McKean et al. | 430/192 |
| 5,501,936 | 3/1996 | Hosoda et al. | 430/191 |
| 5,532,107 | 7/1996 | Oie et al. | 430/192 |
| 5,541,033 | 7/1996 | Blakeney et al. | 430/192 |

FOREIGN PATENT DOCUMENTS

| | | | |
|---|---|---|---|
| 195986 | 3/1989 | European Pat. Off. | C03F 7/10 |
| 1 073 098 | 6/1967 | United Kingdom . | |

OTHER PUBLICATIONS

Database WPI, Section Ch, Week 7620, Derwent Publications Ltd., Class A89, AN 76–36548X XP002068176 and Japan 51 036 932 A (Unitika Ltd.) (abstract).

Database WPI, Section Ch, Week 7730, Derwent Publications Ltd., Class E19, AN 77–52765Y XP002068177 and Japan 52 018 320 A (Hitachi Ltd.) (abstract).

Wen–An Loong et al: Enchanced Oxygen Reactive Ion Etching Resistance of Diazonaphthoquinone–Poly(formyloxystyrene) Resist System by Photoactid Catalyzed Photo–Fries Rearrangement and Potassium Ion Treatment in Aqueous solution Microelectronic Engineering, vol. 13, No. 1 / 04, 1 Mar. 1991, pp. 101–104.

Derwent Abstract, Japanese 3079670, Nippon Kayaku KK, Aug. 23, 1989.

Derwent Abstract, Japanese 2061640, Toshiba KK, Aug. 26, 1988.

"Diazocyclopentadiene" by W. von E. Doering and C. H. DePuy, The Journal of the American Chemical Society, vol. 75, pp. 5955–5957, May 8, 1953.

*Primary Examiner*—Randy Gulakowski
*Attorney, Agent, or Firm*—Sangya Jain

[57] ABSTRACT

The present invention relates to novel photosensitive quinolone compounds, specifically novel 3-diazo 2,4-quinolinedione compounds, that may be used in a variety of applications, such as, photosensitive coating compositions, pharmaceuticals, agricultural, amongst others. The invention further relates to a process for making the novel photosensitive 3-diazo 2,4-quinolinedione compounds. These compounds are particularity useful as a photoactive component in a positive working photoresist composition, particularity for use as a deep ultraviolet (UV) photoresist.

9 Claims, No Drawings

PHOTOSENSITIVE QUINOLONE COMPOUNDS AND A PROCESS OF PREPARATION

FIELD OF INVENTION

The present invention relates to novel photosensitive quinolone compounds, specifically novel 3-diazo 2,4-quinolinedione compounds, that may be used in a variety of applications, such as, photosensitive coating compositions, pharmaceuticals, agricultural, amongst others. The invention further relates to a process for making the novel photosensitive 3-diazo 2,4-quinolinedione compounds. These compounds are particularity useful as a photoactive component in a positive working photoresist composition, particularity for use as a deep ultraviolet (UV) photoresist.

BACKGROUND OF THE INVENTION

Photosensitive compositions are currently used in microlithography to form integrated circuits. These photosensitive compositions typically comprise a photoactive compound, a resin and a solvent. A coating of the photosensitive composition is formed on a substrate, the coating is imagewise exposed and developed to form an image in the coating. As the requirement for faster integrated circuits grows, so does the need to reduce the dimensions of the features printed on these circuits. One method of producing small features is to imagewise irradiate the photoresist with light of shorter wavelengths. The traditional photosensitive compositions which contained novolaks as resins and diazonaphthoquinones as photosensitive compounds worked well at wavelengths between 350 nm and 450 nm. However, with light of wavelengths less than 350 nm, and especially less than 250 nm, neither do the typical novolacs have sufficient transparency, nor do the diazonaphthoquinones have the necessary absorption characteristics to allow for photoresist images of adequate resolution and edge acuity to be formed. Therefore, it has become necessary to synthesize new resins and new photoactive compounds for use at shorter wavelengths.

Diazonaphthoquinone photoactive compounds used for irradiation wavelengths between 350 nm and 450 nm are known and described in the following patents, U.S. Pat. No. 4,588,670, U.S. Pat. No. 4,853,315, U.S. Pat. No. 5,501,936, U.S. Pat. No. 5,532,107 and U.S. Pat. No. 5,541,033, which are incorporated herein by reference.

Radiation-sensitive mixtures containing photoactive diazo derivatives which are suitable for irradiation with high-energy deep UV radiation have been described in the literature for some time.

U.S. Pat. No. 4,339,522 discloses positive-working radiation-sensitive mixtures which contain, as a photoactive compound, a diazo derivative of Meldrum's acid. This compound is said to be suitable for exposure to high-energy UV radiation in the range between 200 nm and 300 nm. However, this photoactive compound is lost under the elevated processing temperatures frequently employed in practice; the radiation-sensitive mixture loses its original activity, so that reproducible photoresist images are not obtained.

Further, positive-working photoactive compounds which are sensitive in the deep UV region are disclosed in U.S. Pat. No. 4,735,885. The compounds have the disadvantage that the carbenes formed from these on exposure do not have adequate stability in the matrix for the desired formulation of carboxylic acid. This results in an inadequate solubility difference between the exposed and the unexposed areas in the developer and thus leads to an undesirably high removal rate of the unexposed areas, leading to poor resolution.

U.S. Pat. No. 4,622,283 provide 2-diazocyclohexane-1,3-dione or -cyclopentane-1,3-dione derivatives as photoactive compounds for radiation-sensitive mixtures of the type described. These compounds have lower volatility, but they exhibit, depending on the substitution pattern present, poor compatibility in the radiation-sensitive mixture. This can cause recrystallization in the solution or in the coating.

EP-A 0 195 986 proposes phosphoryl-substituted diazocarbonyl compounds as photoactive compounds, since these have a higher carbene stability. In practice, however, such compounds will probably not be widely accepted since phosphorus atoms are potentially used as dopants for the semiconductor substrates.

Photoactive compounds based on 3,diazo 4,oxo coumarin structure and sensitive in the shorter wavelengths are disclosed in JP 2,061,640. Additionally, JP 3,079,670, describes a photoresist based on a similar coumarin structure, and further includes 2-diazo 1-indanone and 3-diazo 2,4-quinolinedione as photosensitive compounds, wherein the photoresist when processed gives a negative image. These are monomeric diazo compounds that have substituents of low molecular weight, such as methyl, chlorine, methoxy, propyl, that can be susceptible to volatility, diffusion through the photoresist film, amongst other factors. Furthermore, the 3-diazo 2,4-quinolinedione described in JP 3,079,670 discloses as substituents only sulfonic acid, sulfonylhalogeno, alkoxy, hydrogen or halo groups and when processed in a photoresist composition gives negative images.

All of the references mentioned herein are incorporated by reference in their entirety.

The present invention describes a novel photoactive 3-diazo 2,4-quinolinedione compounds, where one of the benzyl substituents is a carbon containing organic ballast moeity that has a molecular weight greater than 75, and can provide solubility and stability to the novel photoactive compound in a photosensitive composition and its coating during lithographic processing. The invention further discloses a process for the preparation of the novel 3-diazo 2,4-quinolinedione compounds.

SUMMARY OF THE INVENTION

The present invention describes a novel 3-diazo 2,4-quinolinedione photosensitive compound based on the structure

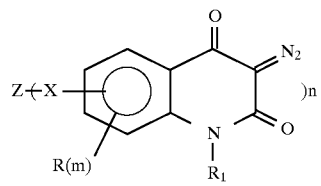

where, $R_1$ is H, alkyl, substituted alkyl, aryl or aralkyl,

R is independently H, alkyl, alkoxy, aryl, aralkyl, halo or fluoroalkyl,

X is a connecting group selected from a group consisting of $SO_2$, CO, O or $NR_1$, Z is a carbon containing organic ballast moeity having molecular weight greater than 75 and can form a bond with the connecting group, m=1–3 and n≧1.

The invention further provides for a process for preparing such a novel compound comprising the steps of:

a) providing a quinolone compound having the formula:

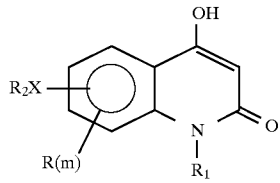

where, $R_1$ is H, alkyl, substituted alkyl, aryl or aralkyl,

R is independently H, alkyl, alkoxy, aryl, aralkyl, halo or fluoroalkyl,

X is a connecting group selected from a group consisting of $SO_2$, $NR_1$ or CO, $R_2$ is H or OH, alkali oxide or alkali salt, and m=1–3;

b) subjecting the quinolone compound to diazo transfer in the presence of a diazo transfer agent to form a 3-diazo 2,4-quinolinedione compound;

c) halogenating the 3-diazo 2,4-quinolinedione compound using a halogenating agent to give a halogenated 3-diazo 2,4-quinolinedione compound of a formula:

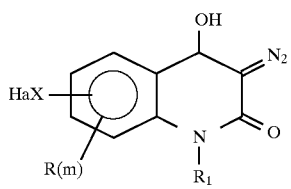

where, $R_1$ is H, alkyl, substituted alkyl, aryl or aralkyl,

R is independently H, alkyl, alkoxy, aryl, aralkyl, halo or alkylfluoro,

Ha is Cl, Br or I

X is a connecting group selected from a group consisting of $SO_2$, $NR_1$ or CO, and m=1–3;

d) reacting the halogenated 3-diazo 2,4-quinolinedione with Z-H, where Z is a ballast moiety described below, in the presence of a base to form the photosensitive 3-diazo 2,4-quinolinedione compound of the formula:

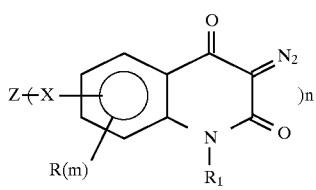

where, $R_1$ is H, alkyl, substituted alkyl, aryl or aralkyl,

R is independently H, alkyl, alkoxy, aryl, aralkyl, halo or fluoroalkyl,

X is a connecting group selected from a group consisting of $SO_2$, CO, O or $NR_1$, Z is a carbon containing organic ballast moeity having molecular weight greater than 75 and can form a bond with the connecting group, m=1–3, and n≧1.

DESCRIPTION OF THE INVENTION

The present invention describes photoactive novel compounds that absorb ultraviolet radiation at wavelengths below 350 nm, and after absorption of the radiation these compounds rearrange and react to give compounds that are less absorbing at the irradiation wavelengths, which provides for a very useful photosensitive component for photoresists, especially deep uv photoresists. The invention further provides for a process for preparing these compounds.

The photoactive compounds of the invention are 3-diazo 2,4-quinolinedione compounds, based on the structure:

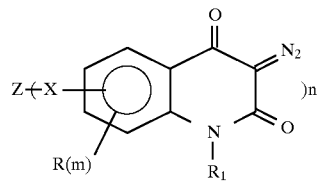

where, $R_1$ is H, alkyl, substituted alkyl, aryl or aralkyl,

R is independently H, alkyl, alkoxy, halo or fluoroalkyl,

X is a connecting group selected from a group consisting of $SO_2$, CO, O or $NR_1$, Z is a carbon containing organic ballast moeity that has molecular weight greater than 75 and can form a bond with the connecting group, m=1–3, and n≧1.

In the above definition and throughout the present specification, alkyl means linear and branched alkyl having the desirable number of carbon atoms and valence. Furthermore, alkyl also includes aliphatic cyclic groups, which may be monocyclic, bicyclic, tricyclic and so on. Suitable linear alkyl groups include methyl, ethyl, propyl, butyl, pentyl, etc.; branched alkyl groups include isopropyl, iso or tert butyl, branched pentyl, hexyl, octyl, etc; monocyclic alkyl groups include cyclopentyl, cyclohexyl and cycloheptyl; bicyclic alkyl groups include substituted bicyclo[2.2.1]heptane, bicyclo[2.2.1]octane, bicyclo [2.2.2] octane, bicyclo [3.2.1]octane, bicyclo [3.2.2]nonane, and bicyclo [3.3.2]decane, and the like. Examples of tricyclic alkyl groups include tricyclo[5.4.0.0.$^{2,9}$]undecane, tricyclo [4.2.1.2.$^{7,9}$]undecane, tricyclo[5.3.2.0.$^{4,9}$]dodecane, and tricyclo[5.2.1.0.$^{2,6}$]decane. As mentioned herein the cyclic alkyl groups may have any of the alkyl alkoxy, ester, hydroxyl or halo groups as substituents.

Other alkyl substituents envisioned as being within the scope of this invention are divalent groups such as methylene, 1,1- or 1,2-ethylene, 1,1-, 1,2-, or 1,3 propylene and so on; a divalent cyclic alkyl group may be 1,2- or 1,3-cyclopentylene, 1,2-, 1,3-, or 1,4-cyclohexylene, and the like. A divalent tricyclo alkyl groups may be any of the tricyclic alkyl groups mentioned herein above. A particularly useful tricyclic alkyl group in this invention is 4,8-bis (methylene)-tricyclo[5.2.1.0.$^{2,6}$]decane.

Aryl substituents include unsubstituted or alkyl, alkoxy, hydroxyl, ester or halo substituted aryl groups, such as, phenyl, tolyl, bisphenyls, trisphenyls, phenylenes, biphenylenes, and others. Fluoroalky groups may be linear or branched and can be represented by trifluoromethyl, 1,1,2-trifluoroethyl, pentafluoroethyl, perfluoropropyl, perfluorobutyl, and 1,1,2,3,3-pentafluorobutyl. Alkoxy substituents can include methoxy, ethoxy, n-propoxy, isopropoxy, n-butoxy, isobutoxy, tert-butoxy, pentyloxy, hexyloxy, heptyloxy, octyloxy, nonanyloxy, decanyloxy, 4-methyihexyloxy, 2-propylheptyloxy, 2-ethyloctyloxy, phenoxy, tolyloxy, xylyloxy, phenylmethoxy, amongst others.

The connecting group, X, is a reactive functionality that can link the diazo containing residue to the carbon containing ballast moiety, Z, and furthermore, X can be represented by groups such as $SO_2$, $CO$, $NR_1$ or oxygen and X can be in 5,6,7 or 8 position of the diazo residue. In one prefered embodiment of the invention, X is in the 6 position of the diazo residue.

The ballast moiety of the photoactive compound described in this invention is a compound that is substantially transparent at the irradiation wavelength and is capable of reacting with the diazo containing residue to give a product that is stable in the photoresist composition and coated photoresist film. The appropriate choice of the ballast moeity is critical to properties of the photoactive compound. In particular, when the photoactive compound of this invention is mixed with an appropriate resin and and an appropriate solvent, and coated onto a substrate and processed to give an image, the solubility and stability of the photoactive compound is essential to the final performance of the photoresist. The carbon containing organic ballast compound, Z, may be selected from a group consisting of a polymer having an oxygen or nitrogen pendant group, and a ballast group having a formula: $(R_3\text{-})_n$, $R_3\text{-}(O)_n$, $R_3\text{-}(CO)_n$, $R_3\text{-}(CO_2)_n$, $R_3\text{-}(R_4N)_n$ or $R_5(SO_2)_n$, where $R_3$ to $R_5$ are independently alkyl having greater than about 6 carbon atom, aryl or aralkyl and n is the degree of diazotization.

Ballast compounds $Z\text{-}R_6$, where Z is the ballast moeity and $R_6$ is H, OH, Cl or Br, that are within the scope of this invention, but not limited to, are hydroxybenzophenones, such as 4,4' dihydroxybenzophenone, 2,3,4 trihydroxybenzophenone, 2,3,4,4' tetrahydroxybenzophenone, etc.; phenolic compounds, such as, bisphenol A, trishydroxyphenylalkanes, phenolic oligomers, trischloroformates of trishydroxy phenyl alkanes or, trihydroxy benzophenones, tetrahydroxy benzophenones, polyhydroxyphenylsulphones, pyrogallols, resorcinols, cresols, phenols, phthaloyl halide, 1,3,5 benzenetricarboxyl halide, etc.; aliphatic compounds containing hydroxy and/or amino functionality, such as, 4,8-biscarbonyl-tricyclo [5.2.1.0.$^{2,6}$]decane, 4,8-bis(chlorocarbonyl)-tricyclo [5.2.1.0.$^{2,6}$]decane, polymers containing hydroxy or amino pendant groups, such as poly4-hydroxystyrene, poly(2-hydroxystyrene 4-hydroxystyrene), copolymers of hydroxystyrene and a member selected from a group consisting of acrylate, methacrylate and mixtures thereof, poly (hydroxystyrene-co-t-butylcarbonyloxystyrene), poly (hyroxystyrene-co-hydroxymethylstyrene), poly (hyroxystyrene-co-acetoxymethylstyrene), alkyl substituted polyvinylphenols, polymers and copolymers of acrylic acid, vinyl alcohol, maleimide, maleic anhydride etc.

The molecular weight of the ballast moiety is greater than 75 and preferably an organic group containing greater than six carbon atoms, more preferably greater than 150, and most preferably greater than 175. Generally the value of n, that is, the degree of diazotization of the ballast group, is preferably greater than 1. In a polymer the degree of diazotization can be significantly larger than 1 and is largely dependent on both the solubility of the diazotized polymer in the photoresist solvent and also its lithographic performance.

The present invention further provides a process for preparing novel photosensitive 3-diazo 2,4-quinolinedione compounds comprising the steps of:

a) providing a quinolone compound having the formula:

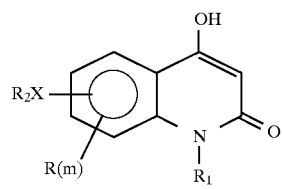

where, $R_1$ is H, alkyl, substituted alkyl, aryl or aralkyl,

R is independently H, alkyl, alkoxy, aryl, aralkyl, halo or fluoroalkyl,

X is a connecting group selected from a group consisting of $SO_2$, CO, O or $NR_1$, $R_2$ is H, OH, alkali oxide or alkali salt, and m=1–3;

b) subjecting the quinolone compound to diazo transfer in the presence of a diazo transfer agent to form a 3-diazo 2,4-quinolinedione compound;

c) halogenating the 3-diazo 2,4-quinolinedione compound using a halogenating agent to give a halogenated 3-diazo 2,4-quinolinedione compound of a formula:

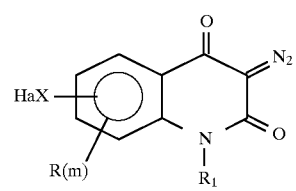

where, $R_1$ is H, alkyl, substituted alkyl, aryl or aralkyl,

R is independently H, alkyl, alkoxy, aryl, aralkyl, halo or fluoroalkyl,

Ha is Cl, Br or I,

X is a connecting group selected from a group consisting of $SO_2$, O, $NR_1$ or CO, and m=1–3;

d) reacting the halogenated 3-diazo 2,4-quinolinedione with Z-H, where Z is a ballast moeity described below, in the presence of a base to form the photosensitive 3-diazo 2,4-quinolinedione compound of the formula:

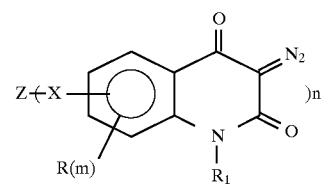

where, $R_1$ is H, alkyl, substituted alkyl, aryl or aralkyl,

R is independently H, alkyl, alkoxy, aryl, aralkyl, halo or fluoroalkyl,

X is a connecting group selected from a group consisting of $SO_2$, CO, O or $NR_1$, Z is a carbon containing ballast moeity having molecular weight greater than 75 and can form a bond with the connecting group, m=1–3, and n≧1.

In another embodiment the invention also provides a process for preparing photosensitive 3-diazo 2,4-quinolinedione compounds comprising the steps of:

a) providing a quinolone compound having the formula:

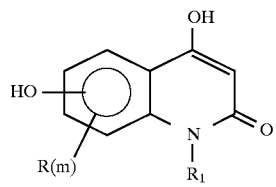

where, $R_1$ is H, alkyl, substituted alkyl, aryl or aralkyl,

R is independently H, alkyl, alkoxy, aryl, aralkyl, halo or fluoroalky, and m=1–3;

b) providing a ballast compound Z-Ha, where Z is the carbon containing organic moeity having molecular weight greater than 75 and can form a bond with the connecting group, and Ha is Cl, Br, I or anhydride;

c) condensing the compound from a) and b) in the presence of a base to form the product with the formula,

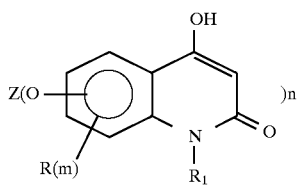

where $R_1$ is H, alkyl, substituted alkyl, aryl or aralkyl,

R is independently H, alkyl, alkoxy, aryl, aralkyl, halo or fluoroalkyl,

Z is a carbon containing ballast moeity having molecular weight greater than 75 and can form a bond with the connecting group, m=1–3, and n≧1;

d) subjecting the product from c) to diazo transfer in the presence of a diazo transfer agent to form a 3-diazo 2,4-quinolinedione compound of the formula:

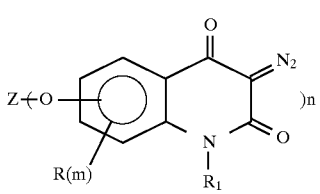

where, $R_1$ is H, alkyl, substituted alkyl, aryl or aralkyl,

R is independently H, alkyl, alkoxy, aryl, aralkyl, halo or fluoroalkyl,

Z is a carbon containing ballast moeity having molecular weight greater than 75 and can form a bond with the connecting group, m=1–3, and n≧1.

The starting material, as shown below, may be purchased or synthesized by any of the known techniques.

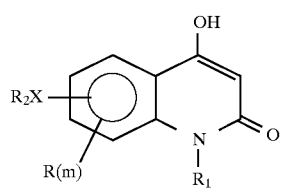

where, R, $R_1$, $R_2$, and X are as defined above. A specific compound, N-methyl-4-hydroxy-6-sulpho-2-quinolone or its salts can be obtained from Dye Star, Charlotte, N.C.

One process step of the invention involves the diazo transfer reaction. This can be done using any reactant capable of transfering the diazo, $N_2$, group to the 3 position of the starting quinolonedione compound. A typical diazo transfer reagent is described by W. Dorring in Journal of American Chemical Society Vol. 75, page 5955 (1953) and incorporated herein by reference. The diazo transfer reaction to the quinolone material requires a stoichiometric amount of the diazo transfer reagent; however, an excess is prefered to take the reaction to completion. Additionally, a base is preferably present in the reaction mixture. Tosyl azide(p-toluenesulfonyl azide) is an example of a diazo transfer reagent. Others may be naphthalene sulfonyl azide, p-carboxybenzene sulfonyl azide, 2,4,6 triisopropyl sulfonyl azide or p-dodecylbenzene sulfonyl azide. Bases that can be used are triethylamine, pyridine, piperidine, sodium hydroxide, sodium carbonate, imidazole and others. The reaction solvent may be acetonitrile, benzene, pentanone, dichloromethane, methanol, amongst others. The temperature of the diazo transfer reaction can range from about 10° C. to about 50° C., preferably from about 20° C. to about 40° C. The reaction is normally carried out at atmospheric pressure, but pressures below and above atmosphere may be used. The time of the reaction varies with the other conditions of temperature and pressure, but can range from 30 minutes to 30 hours. The reaction may be carried out under an inert atmosphere, such as nitrogen.

The halogenation step converts the group on the benzyl residue that contains the hydrogen or hydroxyl end group, for example, N-methyl 3-diazo 6-sulfonic acid 2,4-quinolinedione or its salts, to the corresponding halide. Thus N-methyl 3-diazo 6-sulfonic acid quinolinedione may be converted to N-methyl 3-diazo 6-chlorosulfonate 2,4-quinolinedione. Particular chlorinating agents that may be used, although other halogenating agents may also be used, are thionyl chloride, chlorosulfonic acid, phosgene or phosphorus pentachloride or mixtures thereof; any of these may or may not be in solution. Solvents that may be used, but are not limited to, are chloroform or methylene chloride. The reaction temperature can range from 10° to about 60° C., preferably from about 20° to about 45° C., and the reaction time can range from about 30 minutes to about 4 hours. Upon completion of the reaction the mixture is dropped into an excess of ice to precipitate the product. The product is washed well until the water effluent is pH is 6-7, and dried.

Another step of the process of this invention is the funtionalization of the ballast group to the quinolone or 3-diazo 2,4-quinolonedione. This is carried out by reacting the ballast compound, which has been described previously, with the quinolone or the dione compound. The amount of ballast compound added is dependent on the degree of functionalization desired. This can range from about 5% to about 100%, since the properties of the photoactive compound, especially in a photosensitive composition are determined by the degree of functionalization. The reaction solvent can be any of the typical solvents used for this type of reaction, including butyrolactone, acetone, propyleneglycol monomethyl ether, etc. The reaction time can range from about 30 minutes to about 8 hours. The reaction temperature can range from about 10° to about 40° C., preferably 20° to 30° C.

It is prefered that all the reactions be carried out without white light or sunlight, since the products of the reactions are light sensitive. Typically yellow fluorescent light is prefered.

The following specific examples will provide detailed illustrations of the methods of producing and utilizing the compositions of the present invention. These examples are not intended to limit or restrict the scope of the invention in any way and should not be construed as providing conditions, parameters or values which must be utilized exclusively in order to practice the present invention.

EXAMPLE 1

MATERIALS: The sulfoquinolone (I) was obtained from the Dye Star, Charlotte, N.C., where (I) is the sodium salt of methyl, 4 hydroxy 6-sulfo 2-quinolone.

SYNTHESIS OF TOSYL AZIDE (synthesis taken from Dorring W., J. Am. Chem. Soc. 75, 5955 (1953)

In a 250 ml round bottom flask (RBF) was added 60 ml of deionized (DI) water and 21 g (0.32 mole) of sodium azide. It was mixed at room temperature for 15 minutes until all the sodium azide was in solution. In a 1 liter round bottom flask was added 300 ml of methanol and 50.1 g (0.26 moles) of toluenesulfonyl chloride (tosyl chloride). The solution was mixed at room temperature until all of the tosyl chloride was dissolved. The sodium azide solution was added to the tosyl chloride solution and let mix for 1 hour. The solution darkened and a second phase formed. After the 1 hour hold the reaction was poured into 1200 ml of 20° C. DI water. Two phases formed and the bottom layer was kept. The bottom layer was washed twice with 100 ml of DI water. The yield was 32.4 grams.

EXAMPLE 2

Preparation of the Diazotized Sulfoguinoline (II)

To a 3 necked 1 liter RBF was added 400 ml methanol, 40.7 g ( 0.16 moles) of starting material (I) and 34 g (0.34 moles) of triethylamine. The starting material (I) totally dissolved in the methanol. Tosyl azide 32.4 g (0.16 moles) was added with stirring all at one time. The solution started clear and turned a pinkish brown color. A precipitate was formed. The reaction was stirred for 24 hours at room temperature and the precipitate was filtered off and washed well with 200 ml of methanol. The product was then dried under vacuum at room temperature. The yield was 34 g.

EXAMPLE 3

Preparation of the Diazosulfonyl Chloride of Sulfoguinolinedione (III)

A 3 necked 250 ml RBF was set up with a thermometer and external water bath for either cooling or heating. To the 250 ml RBF was added 50 mL chlorosulfonic acid. Compound 11 (10 g, 0.027 moles) was carefully added to the chlorosulfonic acid keeping the reaction temperature below 30° C. An external water bath was used for cooling the reaction as needed. The reaction/addition was exothermic. After the addition to the chlorosulfonic acid, the reaction was mixed for 30 minutes at 25°–30° C. After 30 minutes, to dissolve Compound II, the reaction was warmed to 45°–50° C. Next, 8.1 g (0.063 moles) of thionyl chloride was added slowly to the reaction using a dropping funnel and maintaining the 45°–50° C. temperature. This step was exothermic. The rate of addition of thionyl chloride was controlled both by the temperature and by the foaming/gas evolution. The reaction was held with stirring for 30 minutes at 45°–50° C. after all of the thionyl chloride had been added. Next, the reaction was cooled to 20° C. The cooled reaction product was carefully and slowly added to 300 g of ice in a 1 liter beaker. As the product was added to the ice/water, the product slurry was stirred. The crude Compound III was filtered and washed well with DI water (2 liter) until the pH was 6–7. The product was rinsed with 250 ml of isopropyl alcohol and dried under vacuum at room temperature. The yield was 7.9 g.

EXAMPLE 4

Diazotized Sulfoquinolinedione Ester Of Tris-1,1,1-(4-Hydroxyphenyl) Ethane (THPE) (lv)

A solution of 2.4 g of 1,4-Diazabicyclo (2,2,2) Octane (Dabco) in 15 ml of gamma Butyrolactone (BLO) was prepared in a 50 ml RBF. To a 100 ml 3 neck RBF was added 3.06 (0.01 moles) of 1,1,1-tris-(4-hydroxyphenyl)ethane (THPE), 5.7 g (0.020 moles) of diazo chloride III, and 30 mL of BLO with magnetic stirring. The reaction was mixed until everything was in solution. The Dabco solution was slowly added to the reaction with stirring keeping the temperature below 30° C. The reaction was stirred for 1 hour at room temperature after the base addition. After the 1 hour hold, 2 ml of glacial acetic acid was added. The reaction was let stand at room temperature for an additional hour. During the 1 hour hold a 200 ml solution of 10% aqueous methanol was prepared. The aqueous methanol was cooled to 10° C. The reaction was filtered through a Whatman #4 filter. The reaction was then drowned into the cooled aqueous methanol with stirring. The aqueous methanol was maintained at 10°–15° C. during the drowning step. The product was filtered and washed well with DI water to minimum conductivity. The product was redissolved in 40 ml of acetone and then drowned into 400 ml of 9% concentrated HCl at 25° C. The product was filtered and washed well until neutrality. It was dried at 40° C. under vacuum. The yield was 5 grams.

A UV spectrum of the solution of the product in acetonitrile was taken before and after irradiation with deep UV light. The compound was shown to absorb in the wavelength range of 220 nm to 285 nm, and upon irradiation the absorption was reduced due to the decomposition.

We claim:

1. A photosensitive compound having a formula:

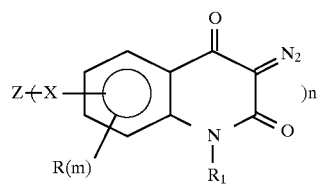

where, $R_1$ is alkyl, aryl or aralkyl,

R is independently H, alkyl, alkoxy, aryl, aralkyl, halo or fluoroalkyl,

X is a connecting group selected from a group consisting of $SO_2$, CO, O or $NR_1$, Z is an organic ballast moeity having molecular weight greater than about 75, m=1–3, and n≧1.

2. The compound according to claim 1, wherein the ballast moeity, Z, is selected from a group consisting of polymer having an oxygen or nitrogen pendant group, and a ballast moeity having the formula: $(R_3\text{-})_n$, $R_3\text{-}(O)_n$, $R_3\text{-}(CO)_n$, $R_3\text{-}(CO_2)_n$, $R_3\text{-}(R_4N)_n$ or $R_5(SO_2)_n$, where $R_3$ to $R_5$ are independently alkyl having greater than 6 carbon atoms, aryl or aralkyl and n is the degree of diazotization.

3. The compound according to claim 2, wherein the ballast moeity is selected from a group consisting of trishydroxyphenylethane, bisphenol A, 4,8-biscarboxyl-tricyclo[5.2.1.0.$^{2,6}$]decane, alkali-soluble resin, novolak resin, poly(4-hydroxystyrene), and poly(co-4-hydroxystyrene-2-hydroxystyrene), copolymers of hydroxystyrene and a member selected from a group of acrylates, methacrylates and mixtures thereof, poly(hydroxystyrene-co-t-butyloxycarbonyloxystyrene); poly(hydroxystyrene-co-hydroxymethylstyrene); poly(hydroxystyrene-co-acetoxymethylstyrene); and alkyl substituted polyvinyl phenols.

4. The compound according to claim 1, wherein Z has greater than six carbon atoms.

5. The compound according to claim 1, wherein Z has a molecular weight greater than about 150.

6. The compound according to claim 1, wherein Z has a molecular weight greater than about 175.

7. The compound according to claim 1, wherein $R_1$ is methyl.

8. The compound according to claim 1, wherein $R_1$ is methyl and X is $SO_2$.

9. The compound according to claim 1, wherein X is in the 6 position.

* * * * *